US012595372B2

(12) United States Patent
Xie et al.

(10) Patent No.: US 12,595,372 B2
(45) Date of Patent: Apr. 7, 2026

(54) HIGH-HYDROPHOBIC, LOW-BLEEDING COLOR LAKE POWDER, METHOD FOR PREPARING SAME AND USE THEREOF

(71) Applicant: SHANGHAI CO-FUN BIOTECH CO., LTD., Shanghai (CN)

(72) Inventors: Xu Xie, Shanghai (CN); Rongmin Kang, Shanghai (CN); Xiaohui Liu, Shanghai (CN); Jianjun Wu, Shanghai (CN)

(73) Assignee: SHANGHAI CO-FUN BIOTECH CO., LTD., Shanghai (CN)

( * ) Notice: Subject to any disclaimer, the term of this patent is extended or adjusted under 35 U.S.C. 154(b) by 863 days.

(21) Appl. No.: 17/765,835

(22) PCT Filed: Sep. 30, 2021

(86) PCT No.: PCT/CN2021/122189

§ 371 (c)(1),
(2) Date: Mar. 31, 2022

(87) PCT Pub. No.: WO2022/078231

PCT Pub. Date: Apr. 21, 2022

(65) Prior Publication Data

US 2023/0183490 A1    Jun. 15, 2023

(30) Foreign Application Priority Data

Oct. 13, 2020    (CN) .......................... 202011087797.5

(51) Int. Cl.
| | |
|---|---|
| *C09B 63/00* | (2006.01) |
| *A61K 8/58* | (2006.01) |
| *C09B 67/00* | (2006.01) |
| *C09B 67/06* | (2006.01) |

(52) U.S. Cl.
CPC ................ *C09B 63/00* (2013.01); *A61K 8/58* (2013.01); *C09B 67/0003* (2013.01); *C09B 68/20* (2013.01); *A61K 2800/432* (2013.01)

(58) Field of Classification Search
CPC ..... C09B 63/00; C09B 67/0003; C09B 68/20; C09B 63/005; C09B 67/0066; A61K 8/58; A61K 2800/432; A61K 8/0241; A61K 8/29; A61K 8/361; A61K 2800/43; A61K 2800/622; A61K 2800/623; A61Q 1/06; A61Q 1/10; A61Q 19/00
See application file for complete search history.

(56) References Cited

U.S. PATENT DOCUMENTS

| | | | | |
|---|---|---|---|---|
| 6,533,858 B1 * | 3/2003 | Cacace | ................. | C09C 1/0015 |
| | | | | 106/499 |
| 6,685,961 B1 | 2/2004 | Gennadios et al. | | |
| 2015/0118494 A1 * | 4/2015 | Vilner | .................. | C09C 1/3684 |
| | | | | 524/576 |
| 2019/0315970 A1 * | 10/2019 | Kameya | .................... | C09C 3/12 |

FOREIGN PATENT DOCUMENTS

| | | | |
|---|---|---|---|
| CN | 102863818 A | | 1/2013 |
| CN | 102863818 B | | 5/2014 |
| CN | 108272648 A | | 7/2018 |
| CN | 108272648 B | | 6/2020 |
| CN | 112358741 A | | 2/2021 |
| EP | 1337245 A2 | | 8/2003 |
| JP | S58-213055 A | | 12/1983 |
| JP | H06136002 A | | 5/1994 |
| JP | 09104833 A | * | 4/1997 |
| JP | 2001206712 A | | 7/2001 |
| JP | 2001294769 A | * | 10/2001 |
| JP | 2002160913 A | * | 6/2002 |
| JP | 2004315378 A | * | 11/2004 |
| JP | 2014240479 A | | 12/2014 |
| JP | 2022135826 A | | 9/2022 |
| KR | 10-2016-0025218 | * | 8/2010 |
| KR | 10-2013-006507 | * | 6/2013 |

OTHER PUBLICATIONS

Full machine English language translation of Xie et al, CN 108272648B, Jul. 13, 2018. (Year: 2024).*
English machine translation of Yang Da Hae et al, KR 10-2013-0060507A, Jun. 10, 2013. (Year: 2025).*
English machine translation of Yang Da Hae et al, KR 10-2016-0025218A, Jun. 10, 2013. (Year: 2025).*
English machine translation of Ichinohe S, JP-09104833-A, Apr. 22, 1997. (Year: 2025).*
English machine translation of Ishikawa T, JP-2002160913-A, Jun. 4, 2002. (Year: 2025).*
English machine translation of JP-2004315378-A, Inokubo T, Nov. 11, 2004. (Year: 2025).*
English machine translation of JP-2001294769-A, Funakura S, Oct. 23, 2001. (Year: 2025).*
Machine English translation including Google-assisted translation of Tables 1 and 4, of Inokubo et al, JP 2004-315378A, Nov. 11, 2004. (Year: 2004).*
European search report of EP21870572.1.

(Continued)

*Primary Examiner* — Coris Fung
*Assistant Examiner* — Caroline D. Liott

(57) ABSTRACT

A high-hydrophobic, low-bleeding color lake powder, a method for preparing the same and a use thereof are provided. A color lake powder is dispersed into water, and a pH value of a system is adjusted to a range of 4 to 5.5. Then surface treating agents such as a silane coupling agent, a titanate coupling agent, a hydrogenated lecithin and an aliphatic acid are used to modify the color lake powder. Then pulverizing and drying the resultant to obtain the modified color lake powder.

8 Claims, No Drawings

(56)          References Cited

OTHER PUBLICATIONS

Notice of Reasons for Refusal—JP2022518370.
International Search Report of PCT/CN2021/122189.
China Office Action of 202011087797.5.

\* cited by examiner

HIGH-HYDROPHOBIC, LOW-BLEEDING COLOR LAKE POWDER, METHOD FOR PREPARING SAME AND USE THEREOF

CROSS-REFERENCE TO RELATED APPLICATION

This application is a National Stage application of International Application No. PCT/CN2021/122189 filed on Sep. 30, 2021, which claims all benefits accruing from China Patent Application No. 202011087797.5, filed on Oct. 13, 2020, in the China National Intellectual Property Administration, and titled "HIGH-HYDROPHOBIC, LOW-BLEEDING COLOR LAKE POWDER, METHOD FOR PREPARING SAME AND USE THEREOF", both of which are hereby incorporated by reference.

TECHNICAL FIELD

The present disclosure relates to a field of cosmetic raw material, in particular to a high-hydrophobic, low-bleeding color lake powder, a method for preparing same and a use thereof.

BACKGROUND

With improvement of living standards in modern society, people's demand for cosmetics is also growing rapidly. Pigments are essential in many cosmetic products such as lipsticks and eye shadows. However, solubility of pigments is essential to the use and durability of pigment-containing cosmetic products, and if not great, it may even bring hidden dangers to health of users.

After combining a water-soluble organic pigment with an inorganic matrix, a color lake powder which has both a bright color of the organic pigment and a safety and stability of the inorganic substance can be prepared. Thus, the originally water-soluble raw materials can be greatly dispersed in an oil phase, resulting in products that are more convenient to use and have a longer-lasting color. People have also tried to treat the color lake powder via modifiers to further improve the lipophilicity of the color lake powder. However, in an actual test process, it is found that although the color lake powder has good lipophilicity, the hydrophobicity of which has not been improved. Therefore, the color lake powder is easy to drop off from a user's face due to sweating and the like. Moreover, for some special cosmetics such as lipsticks, if the color lake powder in the cosmetics is not hydrophobic, they may also be brought into the human body via diet due to the dissolution of pigments, resulting in a potential safety hazard. In addition, the color lake powder has a problem of color bleeding, which also greatly reduces using experience of the user.

SUMMARY

In view of this, it is necessary to provide a high-hydrophobic and low-bleeding color lake powder, a method for preparing the same and a use thereof.

In an aspect of the present disclosure, a method for preparing a color lake powder is provided, which includes the following steps: dispersing a color lake powder in water, and adjusting a pH value of a reacting system to an range of 4 to 5.5 to obtain a first mixture; and conducting process a) or a') as following. Process a) includes: step a1) mixing a first surface treating agent and a first alcohol solvent uniformly to obtain a pre-mixture, adding the pre-mixture into the first mixture, and blending thereof to modify the color lake powder, so as to obtain a second mixture, wherein the first surface treating agent includes at least one selected from a silane coupling agent, a titanate coupling agent, and a hydrogenated lecithin; and step a2), separating a solid phase from the second mixture, washing, drying and pulverizing the solid phase to obtain a modified color lake powder. Process a') includes: step a1'), separating a solid phase from the first mixture, washing, drying, and pulverizing the solid phase to obtain a powder; and step a2'), mixing a second surface treating agent and a second alcohol solvent to obtain a third mixture, evenly spraying the third mixture on the powder to modify the color lake powder under a condition of stirring, and drying the sprayed powder to obtain a modified color lake powder. The second surface treating agent includes at least one selected from a silane coupling agent, a titanate coupling agent, and an aliphatic acid.

In some embodiments, in step a1), a mass of the first surface treating agent is 2% to 10% of a mass of the color lake powder.

In some embodiments, in step a2'), a mass of the second surface treating agent is 2% to 10% of a mass of the color lake powder.

In some embodiments, a mass of the color lake powder is less than or equals to 30% of a mass of water.

In some embodiments, in step a1), the first alcohol solvent includes at least one selected from ethanol and isopropanol; and/or, a ratio of a mass of the first surface treating agent and a mass of the first alcohol solvent is in a range of 1:1 to 1:1.5.

In some embodiments, in step a2'), the second alcohol solvent comprises at least one selected from ethanol and isopropanol; and/or, a ratio of a mass of the second surface treating agent and a mass of the second alcohol solvent is in a range of 1:1 to 1:1.5.

In some embodiments, an operation temperature of dispersing the color lake powder in water and adjusting the pH value to the range of 4 to 5.5 is in a range of 60 degrees centigrade to 80 degrees centigrade, In some embodiments, in process a), an operation temperature before separating the solid phase from the second mixture is in a range of 60 degrees centigrade to 80 degrees centigrade.

In some embodiments, in step a2), washing the solid phase until an electric conductivity of a washing solution is less than 50 μS/cm.

In some embodiments, in step a1'), washing the solid phase until an electric conductivity of a washing solution is less than 50 μS/cm.

In some embodiments, in process a), a rotating speed of the stirring is in a range of 300 r/min to 500 r/min, and a time of the stirring is in a range of 100 min to 140 min.

In some embodiments, in step a'), a rotating speed of the stirring is in a range of 5000 r/min to 20000 r/min.

In some embodiments, in process a), a drying temperature is in a range of 80 degrees centigrade to 120 degrees centigrade; and/or, in step a'), a temperature for drying the solid phase and/or the sprayed powder is in a range of 80 degrees centigrade to 120 degrees centigrade.

In the present disclosure, by controlling a pH value of a color a dispersion liquid containing a color lake powder in a range of 4 to 5.5, chemical structures of chemical bonds of the color lake powder may not be damaged. When a method including the process a) is used, a hydrolytic process of a first surface treating agent or a mixture thereof can be facilitated, so that the color lake powder and the first surface treating agent can react more completely under the condition, so as to obtain a modified color lake powder with good hydrophobicity. The first surface treating agent can be silane coupling agent, titanate coupling agent, hydrogenated lecithin, and the like. When a method including the process a) or a') is used, for some basic color lake powders, the method can facilitate forming hydrogen bonds, so that the color lake powder can combine with a first/second surface treating agent and dehydrate, so as to modify the basic color lake powder. At the same time, a color lake powder prepared by a conventional art can be easy to bleed/separate out. The color lake powder prepared by the method in the present disclosure can be not easy to separate out/bleed while using, thereby improving safety of the color lake powder and stability thereof in an emulsification system.

In another aspect of the present disclosure, a color lake powder prepared by the above method is provided, a contact angle of water of the color lake powder is larger than or equal to 133°.

The present disclosure further provides a cosmetic product containing the color lake powder prepared by the above method.

DETAILED DESCRIPTION

In order to facilitate understanding the present disclosure, the present disclosure will be more fully described below with reference to the relevant embodiments. However, the present disclosure may be implemented in many different forms and is not limited to the embodiments described herein. Rather, these embodiments are provided so that a thorough and complete understanding of the disclosure of the present disclosure is provided.

In addition, the terms "first" and "second" are only used for descriptive purposes, and cannot be understood as indicating or implying relative importance or implying the number of indicated technical features. Thus, a feature delimited with "first", "second" may expressly or implicitly include at least one of that features. In the description of the present disclosure, "plurality" means at least two, such as two, three, etc., unless expressly and specifically defined otherwise. In the description of this present disclosure, "several" means at least one, such as one, two, etc., unless expressly and specifically defined otherwise.

Unless otherwise defined, all technical and scientific terms used herein have the same meaning as commonly understood by one of ordinary skill in the art to which the present disclosure belongs to. The terms used herein in the specification of the present disclosure are for the purpose of describing specific embodiments only and are not intended to limit the present disclosure. As used herein, the term "and/or" includes any and all combinations of one or more of the associated listed items.

In the present disclosure a high-hydrophobic and low-bleeding color lake powder, a method for preparing the same and a use thereof are provided.

In an aspect of the present disclosure, a method for preparing a color lake powder is provided, which can include the following steps: dispersing a color lake powder in water, and adjusting a pH value of a reacting system to an range of 4 to 5.5 to obtain a first mixture; and conducting process a) or a') as following. Process a) can include: step a1), mixing a first surface treating agent and a first alcohol solvent uniformly to obtain a pre-mixture, adding the pre-mixture into the first mixture, and blending thereof to modify the color lake powder, so as to obtain a second mixture, wherein the first surface treating agent can include at least one selected from a silane coupling agent, a titanate coupling agent, and a hydrogenated lecithin; and then step a2), separating a solid phase from the second mixture, washing, drying and pulverizing the solid phase to obtain a modified color lake powder. Optionally, process a') can include: step a1') separating a solid phase from the first mixture, washing, drying, and pulverizing the solid phase to obtain a powder; and step a2'), mixing a second surface treating agent and a second alcohol solvent to obtain a third mixture, evenly spraying the third mixture on the powder to modify the color lake powder under a condition of stirring, and drying the sprayed powder to obtain a modified color lake powder. The second surface treating agent can include at least one selected from a silane coupling agent, a titanate coupling agent, and an aliphatic acid.

In some embodiments, the pH value can be in a range from 4.1 to 5.2, optionally can be 4.2, 4.4, 4.6, 4.8, 5.0, 5.2 and 5.4. It is important to select a proper range of the pH value of the reacting system. If the pH value is less than 4, a structure of chemical bonds in the color lake powder can be damaged. If the reacting system is faintly acid (higher than 5.5) or even basic, the modifying effect may be largely lowered even structural stability of the color lake powder can be ensured.

A process for treating the color lake powder with the surface treating agent can differ according to characteristics of the surface treating agent. Process a) is a wet method, which can be suitable for surface treating agents having certain dispersibility in water, and modify the color lake powder in water. Step a') is a dry method, which can be suitable for surface treating agents that can be stable at high temperature. At high temperature, the melted surface treating agent and the color lake powder can be mixed relatively uniformly to modify the color lake powder.

In some embodiments, the silane coupling agent can be at least one selected from trimethoxyoctylsilane, triethoxyoctylsilane and hexyltrimethoxysilane.

In some embodiments, the titanate coupling agent can be isopropoxytitanium triisostearate.

In some embodiments, the aliphatic acid can be at least one selected from stearic acid, myristic acid and palmitic acid.

In some embodiments, a mass of the first surface treating agent can be 2% to 10% of a mass of the color lake powder. Optionally, the mass of the first surface treating agent can be 3% to 9% of the mass of the color lake powder. Optionally, can be 4%, 6% or 8% of the mass of the color lake powder. The mass of the first surface treating agent can be directly related to the modifying effect of the color lake powder. If the mass of the first surface treating agent is too small (less than 2%), the modifying effect can be bad. If the mass of the first surface treating agent is too great, in a first aspect, since a capacity of the color lake powder to the first surface treating agent is finite, the modifying effect cannot improve along with increasing of the mass of the first surface treating agent when the mass of the first surface treating agent achieves a certain amount; in a second aspect, unduly large mass of the first surface treating agent may cause adverse effect on the modifying effect, and lowering the hydrophobicity.

In some embodiments, a mass of the second surface treating agent can be 2% to 10% of a mass of the color lake powder. Optionally, the mass of the second surface treating agent can be 3% to 9% of the mass of the color lake powder. Optionally, can be 4%, 6% or 8% of the mass of the color lake powder. The mass of the second surface treating agent can be directly related to the modifying effect of the color lake powder. If the mass of the second surface treating agent is too small (less than 2%), the modifying effect can be bad.

If the mass of the second surface treating agent is too great, in a first aspect, since a capacity of the color lake powder to the second surface treating agent is finite, the modifying effect cannot improve along with increasing of the mass of the second surface treating agent when the mass of the second surface treating agent achieves a certain amount; in a second aspect, unduly large mass of the second surface treating agent may cause adverse effect on the modifying effect, and lowering the hydrophobicity.

In some embodiments, the mass of the color lake powder can be less than or equals to 30% of a mass of water. Optionally, the mass of the color lake powder can be in a range of 5% to 25% of a mass of water. Optionally, the mass of the color lake powder can be 10%, 15% or 20% of a mass of water. The mass of the color lake powder should not be too high, or the reacting system may be too thick to disperse the color lake powder and the first/second surface treating agent, thereby affecting the modifying effect.

In some embodiments, the water can be deionized water.

In some embodiments, the first/second alcohol solvent can be at least one selected from ethanol and isopropanol. Use of the first/second alcohol solvent can facilitate improving dispersity of the first/second surface treating agent in water, so that the first/second surface treating agent can be better mixed with the color lake powder, thereby modifying the color lake powder.

In some embodiments, in step a1) a ratio of a mass of the first surface treating agent and a mass of the first alcohol solvent is in a range of 1:1 to 1:1.5. In some embodiments, in step a2'), a ratio of a mass of the second surface treating agent and a mass of the second alcohol solvent is in a range of 1:1 to 1:1.5.

In some embodiments, an operation temperature of dispersing the color lake powder in water and adjusting the pH value of the reacting system to the range of 4 to 5.5 can be in a range of 60 degrees centigrade to 80 degrees centigrade.

In some embodiments, in step a2), an operation temperature before separating the solid phase from the second mixture can be in a range of 60 degrees centigrade to 80 degrees centigrade.

In some embodiments, in step a2), washing the solid phase until an electric conductivity of a washing solution can be less than 50 μS/cm. In some embodiments, in step a1'), washing the solid phase until an electric conductivity of a washing solution can be less than 50 μS/cm.

In some embodiments, in process a), a rotating speed of the stirring can be in a range of 300 r/min to 500 r/min, and a time of the stirring can be in a range of 100 min to 140 min.

In some embodiments, in step a'), a rotating speed of the stirring can be in a range of 5000 r/min to 20000 r/min.

In some embodiments, in process a), a drying temperature can be in a range of 80 degrees centigrade to 120 degrees centigrade, and a water content of the reacting system after drying can be less than or equal to 5%. Optionally, the drying temperature can be in a range of 110 degrees centigrade to 120 degrees centigrade, or can be any one of 85 degrees centigrade, 90 degrees centigrade, 95 degrees centigrade, 100 degrees centigrade or 105 degrees centigrade.

In some embodiments, in step a'), a temperature for drying the solid phase and/or the sprayed powder can be in a range of 80 degrees centigrade to 120 degrees centigrade. After drying the solid phase, a water content of the reacting system can be less than or equal to 5%. A time for drying the sprayed powder can be in a range of 3 hours to 5 hours. Optionally, the temperature for drying the solid phase and/or the sprayed powder can be in a range of 110 degrees centigrade-120 degrees centigrade, or can be any one of 85 degrees centigrade, 90 degrees centigrade, 95 degrees centigrade, 100 degrees centigrade, 105 degrees centigrade.

In the present disclosure, by controlling a pH value of a color a dispersion liquid containing a color lake powder in a range of 4 to 5.5, chemical structures of chemical bonds of the color lake powder may not be damaged. When a method including the process a) is used, a hydrolytic process of a surface treating agent or a mixture thereof can be facilitated, so that the color lake powder and the surface treating agent can react more completely under the condition, so as to obtain a modified color lake powder with good hydrophobicity. The surface treating agent can be silane coupling agent, titanate coupling agent, hydrogenated lecithin, and the like. When a method including the process a) or a') is used, for some basic color lake powders, the acidizing process can further facilitate forming hydrogen bonds, so that the color lake powder can combine with a surface treating agent and dehydrate, so as to modify the basic color lake powder. At the same time, a color lake powder prepared by a conventional art can be easy to bleed/separate out. The color lake powder prepared by the method in the present disclosure can be not easy to bleed/separate out while using, thereby improving safety of the color lake powder and stability thereof in an emulsification system.

In another aspect of the present disclosure, a color lake powder prepared by the above method can be provided.

The present disclosure can further provide a cosmetic product containing the color lake powder prepared by the above method.

The present disclosure will be further described in conjunction with embodiments and comparative embodiments hereinafter. It should be understood that although the equipment and the raw materials used herein are relatively specific, they are not intended to limit those in other embodiments. For example, the pH value can be not limited to be regulated by hydrochloric acid; and temperature controlling can be not limited to be water bath.

Embodiment 1

(1) 50 g of red 6# barium lake powder was dispersed in 500 g of deionized water, and stirred in a 60 degrees centigrade-water bath for 10 min.

(2) A pH value of the reacting system was regulated to 4.0 with hydrochloric acid.

(3) 2.5 g of triethoxyoctylsilane and 2.5 g of ethanol (95%) were mixed evenly.

(4) A resultant of step (3) was added into a resultant of step (2), and stirred at a speed of 400 r/min and a temperature of 60 degrees centigrade for 120 min.

(5) A resultant of step (4) was subjected to suction filtration and a filter residue was washed until an electric conductivity of a washing solution was less than 50 μS/cm.

(6) The filter residue was dried at a temperature of 115 degrees centigrade until a water content of the filter residue was less than 5%.

(7) The dried filter residue was pulverized to obtain a modified red 6# barium lake powder.

Embodiment 2

The red 6# barium lake powder in embodiment 1 was replaced with red 7# calcium lake powder.

Embodiment 3

The red 6# barium lake powder in embodiment 1 was replaced with red 30# aluminum lake powder.

Embodiment 4

The 50 g of red 6# barium lake powder in embodiment 1 was changed to 150 g of red 6# barium lake powder.

The 2.5 g of triethoxyoctylsilane was changed to 7.5 g of triethoxyoctylsilane, and the 2.5 g of ethanol (95%) was changed to 7.5 g of ethanol (95%).

Embodiment 5

The pH value of the reacting system in embodiment 1 was changed to 5.5.

Embodiment 6

Step (3) included "2.5 g of triethoxyoctylsilane and 2.5 g of ethanol (95%) were mixed evenly" in embodiment 1 was changed to "1.0 g of triethoxyoctylsilane and 1.0 g of ethanol (95%) were mixed evenly".

Embodiment 7

Step (3) included "2.5 g of triethoxyoctylsilane and 2.5 g of ethanol (95%) were mixed evenly" in embodiment 1 was changed to "5.0 g of triethoxyoctylsilane and 5.0 g of ethanol (95%) were mixed evenly".

Embodiment 8

The reacting temperature of step (1) to step (4) in embodiment 1 was changed to 80 degrees centigrade.

Embodiment 9

(1) 50 g of red 6# barium lake powder was dispersed in 500 g of deionized water, and stirred in a 60 degrees centigrade-water bath for 10 min.

(2) A pH value of the reacting system was regulated to 4.0 with hydrochloric acid.

(3) A resultant of step (2) was subjected to suction filtration and a filter residue was washed until an electric conductivity of a washing solution was less than 50 μS/cm.

(4) The filter residue was dried at a temperature of 115 degrees centigrade until a water content of the filter residue was less than 5%.

(5) The dried filter residue was added in a high-speed pulverizer and pulverized. Then a mixture of 2.5 g of triethoxyoctylsilane and 2.5 g of ethanol (95%) was sprayed in at a speed rate of 10000 r/min, and the resultant was stirred evenly.

(7) A resultant of step (6) was dried at 115 degrees centigrade for 4 hours to obtain a modified red 6# barium lake powder.

Embodiment 10

The 2.5 g of triethoxyoctylsilane in step (3) of embodiment 1 was changed to 2.5 g of hexyltrimethoxysilane.

Embodiment 11

The 2.5 g of triethoxyoctylsilane in step (3) of embodiment 1 was changed to 2.5 g of hydrogenated lecithin, and the drying temperature in step (6) was changed to 80 degrees centigrade.

Embodiment 12

The 2.5 g of triethoxyoctylsilane in step (5) of embodiment 9 was changed to 2.5 g of stearic acid.

Embodiment 13

The 2.5 g of triethoxyoctylsilane in step (5) of embodiment 9 was changed to 2.5 g of myristic acid.

Embodiment 14

The 2.5 g of triethoxyoctylsilane in step (5) of embodiment 9 was changed to 2.5 g of palmitic acid.

Embodiment 15

The 2.5 g of triethoxyoctylsilane in step (5) of embodiment 9 was changed to 2.5 g of isopropoxytitanium triisostearate.

Comparative Embodiment 1

(1) 50 g of red 6# barium lake powder was dispersed in 500 g of deionized water, and stirred in a 60 degrees centigrade-water bath for 10 min.

(2) 2.5 g of triethoxyoctylsilane and 2.5 g of ethanol (95%) were mixed evenly.

(3) A resultant of step (2) was added into a resultant of step (1), and stirred at a speed of 400 r/min and a temperature of 60 degrees centigrade for 120 min.

(4) A resultant of step (3) was subjected to suction filtration and a filter residue was washed until an electric conductivity of a washing solution was less than 50 μS/cm.

(5) The filter residue was dried at a temperature of 115 degrees centigrade until a water content of the filter residue was less than 5%.

(6) The dried filter residue was pulverized to obtain a treated red 6# barium lake powder.

Comparative Embodiment 2

The red 6# barium lake powder in comparative embodiment 1 was replaced with red 7# calcium lake powder.

Comparative Embodiment 3

The red 6# barium lake powder in comparative embodiment 1 was replaced with red 30 # aluminum lake powder.

Comparative Embodiment 4

(1) 50 g of red 6# barium lake powder was dispersed in 500 g of deionized water, and stirred in a 60 degrees centigrade-water bath for 10 min.

(2) A pH value of the reacting system was regulated to 4.0 with hydrochloric acid.

(3) 2.5 g of triethoxyoctylsilane was added into a resultant of step (2), and stirred at a speed of 400 r/min and a temperature of 60 degrees centigrade for 120 min.

(4) A resultant of step (3) was subjected to suction filtration and a filter residue was washed until an electric conductivity of a washing solution was less than 50 µS/cm.

(5) The filter residue was dried at a temperature of 115 degrees centigrade until a water content of the filter residue was less than 5%.

(6) The dried filter residue was pulverized to obtain a treated red 6# barium lake powder.

Comparative Embodiment 5

(1) 50 g of red 6 # barium lake powder was added a high-speed homogenizer, and hydrochloric acid with the same amount in embodiment 1 was sprayed in at a speed rate of 10000 r/min, and the resultant was mixed evenly.

(2) Then a mixture of 2.5 g of triethoxyoctylsilane and 2.5 g of ethanol (95%) was sprayed in, and the resultant was stirred evenly.

(3) A resultant of step (2) was dried at 115 degrees centigrade for 4 hours to obtain a treated red 6# barium lake powder.

Comparative Embodiment 6

(1) 50 g of red 6# barium lake powder was added into a Henschel mixer.

(2) 7.5 g of triethoxyoctylsilane and 1.5 g of reactive organic siloxane were mixed evenly.

(3) A resultant of step (2) was added in a resultant of step (1) and reacted for 30 min.

(4) A resultant of step (3) was pulverized at a pulverizing pressure of 4 kg and a classifier rotate speed of 10000 r/min.

(5) A resultant of step (4) was dried at 110 degrees centigrade for 9 hours to obtain a treated red 6# barium lake powder.

Comparative Embodiment 7

The pH value of the reacting system in embodiment 1 was changed to 6.

Comparative Embodiment 8

Step (3) included "2.5 g of triethoxyoctylsilane and 2.5 g of ethanol (95%) were mixed evenly" in embodiment 1 was changed to "0.75 g of triethoxyoctylsilane and 0.75 g of ethanol (95%) were mixed evenly".

Comparative Embodiment 9

Step (3) included "2.5 g of triethoxyoctylsilane and 2.5 g of ethanol (95%) were mixed evenly" in embodiment 1 was changed to "6 g of triethoxyoctylsilane and 6 of ethanol (95%) were mixed evenly".

Hydrophobicity of the products was tested by molding the modified lake powders into cakes, and then testing the contact angle of water of the cakes.

| Group | Contact Angle of Water (°) | Group | Contact Angle of Water (°) |
|---|---|---|---|
| Embodiment 1 | 148 | Comparative Embodiment 1 | 40 |
| Embodiment 2 | 146 | Comparative Embodiment 2 | 100 |
| Embodiment 3 | 150 | Comparative Embodiment 3 | 20 |

-continued

| Group | Contact Angle of Water (°) | Group | Contact Angle of Water (°) |
|---|---|---|---|
| Embodiment 4 | 135 | Comparative Embodiment 4 | 38 |
| Embodiment 5 | 133 | Comparative Embodiment 5 | 45 |
| Embodiment 6 | 140 | Comparative Embodiment 6 | 60 |
| Embodiment 7 | 136 | Comparative Embodiment 7 | 55 |
| Embodiment 8 | 144 | Comparative Embodiment 8 | 90 |
| Embodiment 9 | 138 | Comparative Embodiment 9 | 105 |
| Embodiment 10 | 140 | Red 6 # barium lake | 39 |
| Embodiment 11 | 143 | Red 7 # calcium lake | 100 |
| Embodiment 12 | 135 | Red 30 # Aluminum lake | 20 |
| Embodiment 13 | 137 | / | / |
| Embodiment 14 | 142 | / | / |
| Embodiment 15 | 148 | / | / |

A method for testing the bled pigment included the following steps.

(1) 2.4 g of color lake powder and 9.6 g PAO (Pionier Gel Pao 120) 12 was mixed evenly.

(2) Glycerol and deionized water was mixed evenly in a mass ratio of 1:1.

(3) 10 g of the resultant of step (1) and 30 g of the resultant of step (2) were mixed, and kept in a dark place for 24 hours. Color of the supernatant was observed. If the color of the supernatant was light, the bled pigment was little. If the color of the supernatant was dark, the bled pigment was much.

| Group | Color of the supernatant | Group | Color of the supernatant |
|---|---|---|---|
| Embodiment 1 | Colorless | Comparative Embodiment 1 | Dark |
| Embodiment 2 | Light | Comparative Embodiment 2 | Dark |
| Embodiment 3 | Colorless | Comparative Embodiment 3 | Light |
| Embodiment 4 | Light | Comparative Embodiment 4 | Dark |
| Embodiment 5 | Light | Comparative Embodiment 5 | Pretty Dark |
| Embodiment 6 | Light | Comparative Embodiment 6 | Pretty Dark |
| Embodiment 7 | Light | Comparative Embodiment 7 | Dark |
| Embodiment 8 | Light | Comparative Embodiment 8 | Dark |
| Embodiment 9 | Light | Comparative Embodiment 9 | Dark |
| Embodiment 10 | Light | Red 6 # barium lake | Very Dark |
| Embodiment 11 | Light | Red 7 # calcium lake | Very Dark |
| Embodiment 12 | Light | Red 30 # Aluminum lake | Very Dark |
| Embodiment 13 | Light | / | / |
| Embodiment 14 | Light | / | / |
| Embodiment 15 | Light | / | / |

Color stability of W-emulsification system.

| Phase | Raw Material | Percentage % |
|---|---|---|
| A | PEG-10 dimethyl silicon polymer | 2 |
| | Lauryl Peg-9 Polydimethylsiloxyethyl Dimethicone | 1 |
| | Phenyl Trimethicone | 7 |
| | Caprylic/Capric Triglyceride | 4 |
| | Octyldodecanol | 5 |
| | Butylene Glycol Dicaprylate/Dicaprate | 5 |
| | dimethyl silicon polymer | 2 |
| | C9-12 Alkanes | 6 |
| B | Cyclopentadimethylsiloxane | 15 |
| | Disteardimonium hectorite | 1 |
| C | Water | To 100 |
| | Glycerol | 5 |
| | Magnesium Sulfate | 0.7 |
| | Propylene glycol | 5 |
| | Phenoxyethanol/Ethylhexylglycerin | 0.75 |
| D | Color Lake Powder | 0.25 |

The formulations above were kept in a dark place at normal temperature and in a dark place at 48 degrees centigrade for 10 days, respectively. Color differences between the samples kept at normal temperature and the samples kept at 48 degrees centigrade were observed after 10 days.

| Group | Color Change | Group | Color Change |
|---|---|---|---|
| Embodiment 1 | No Obvious Change | Comparative Embodiment 1 | A Little Lighter |
| Embodiment 2 | No Obvious Change | Comparative Embodiment 2 | A Little Lighter |
| Embodiment 3 | No Obvious Change | Comparative Embodiment 3 | A Little Lighter |
| Embodiment 4 | No Obvious Change | Comparative Embodiment 4 | A Little Lighter |
| Embodiment 5 | No Obvious Change | Comparative Embodiment 5 | Obvious Color fading |
| Embodiment 6 | No Obvious Change | Comparative Embodiment 6 | Obvious Color fading |
| Embodiment 7 | No Obvious Change | Comparative Embodiment 7 | A Little Lighter |
| Embodiment 8 | No Obvious Change | Comparative Embodiment 8 | A Little Lighter |
| Embodiment 9 | No Obvious Change | Comparative Embodiment 9 | A Little Lighter |
| Embodiment 10 | No Obvious Change | Red 6 # barium lake | Obvious Color fading |
| Embodiment 11 | No Obvious Change | Red 7 # calcium lake | Obvious Color fading |
| Embodiment 12 | No Obvious Change | Red 30 # Aluminum lake | Obvious Color fading |
| Embodiment 13 | No Obvious Change | / | / |
| Embodiment 14 | No Obvious Change | / | / |
| Embodiment 15 | No Obvious Change | / | / |

Comparative embodiments 1 to 3 did not include an acidizing process, hydrophobicity of the treated color lake powders was hardly improved, color bleeding phenomena of the treated color lake powders was serious, and stability of the treated color lake powders in an emulsification system was not good. In comparative embodiment 4, the surface treating agent triethoxyoctylsilane was not pre-treated with alcohol solvents. Thus, the surface treating agent had a poor dispersity in water, so that the surface treating agent cannot sufficiently contact with the color lake powder. Therefore, hydrophobicity of the treated color lake powders was not improved, color bleeding of the treated color lake powders was serious, and stability of the treated color lake powders in an emulsification system was not good. In comparative embodiment 5, the color lake powder was acidized, but the surface treating agent was not acidized. Hydrophobicity of the treated color lake powders was slightly improved, color bleeding of the treated color lake powders was serious, and stability of the treated color lake powders in an emulsification system was very bad. In comparative embodiment 6, the color lake powder was treated by a conventional method. Although lipophilicity of the color lake powder was largely improved, hydrophobicity of the treated color lake powders was hardly improved, color bleeding of the treated color lake powders was serious, and stability of the treated color lake powders in an emulsification system was very bad. In comparative embodiment 7, the pH value was not rational. Thus, hydrophobicity, color bleeding and stability in an emulsification system of the treated color lake powder were also influenced. In comparative embodiments 8 and 9, the mass of the surface treating agents was not rational. Firstly, hydrophobicity of the treated color lake powders was finitely improved, color bleeding of the treated color lake powders was not ideally improved, and stability of the treated color lake powders in an emulsification system was not good.

In view of above, the technical features in the present disclosure are of important effect on improving hydrophobicity of color lake powders, improving color bleeding of the color lake powders and improving stability of the color lake powders in an emulsification system.

The technical features of the above-described embodiments may be combined in any combination. For the sake of brevity of description, not all possible combinations of the technical features in the above embodiments are described. However, as long as there is no contradiction between the combinations of these technical features, all should be considered as within the scope of this disclosure.

The above-mentioned embodiments only represent several embodiments of the present disclosure, and the descriptions thereof are relatively specific and detailed, but should not be construed as limiting the scope of the patent present disclosure. It should be pointed out that for one of ordinary skill in the art, without departing from the concept of the present disclosure, several modifications and improvements can be made, which all belong to the protection scope of the present disclosure. Therefore, the scope of protection of the patent of the present disclosure shall be subject to the appended claims.

We claim:

1. A method for preparing a hydrophobic modified color lake powder, comprising:

step 1) dispersing a color lake powder in water, and adjusting a pH value of a reacting system to a range of 4 to 5.5 to obtain a first mixture;

step 2), mixing a first surface treating agent and a first alcohol solvent uniformly to obtain a pre-mixture, adding the pre-mixture into the first mixture, and blending thereof to modify the color lake powder, so as to obtain a second mixture, wherein the first surface treating agent comprises at least one selected from a silane coupling agent, a titanate coupling agent, and a hydrogenated lecithin; and step 3), separating a solid phase from the second mixture, and then washing, drying and pulverizing the solid phase, to obtain the hydrophobic modified color lake powder, wherein the hydrophobic modified color lake powder has a contact angle of water larger than or equal to 133°,

wherein in step 2), a mass of the first surface treating agent is 5% of a mass of the color lake powder, in step 3), an operation temperature before separating the solid phase from the second mixture is in a range of 60 degrees centigrade to 80 degrees centigrade.

2. The method of claim 1, wherein a mass of the color lake powder is less than or equal to 30% of a mass of water.

3. The method of claim 1, wherein in step 2), the first alcohol solvent comprises at least one selected from ethanol and isopropanol; and/or, a ratio of the mass of the first surface treating agent and a mass of the first alcohol solvent is in a range of 1:1 to 1:1.5.

4. The method of claim 1, wherein an operation temperature of dispersing the color lake powder in water and adjusting the pH value of the reacting system to the range of 4 to 5.5 is in a range of 60 degrees centigrade to 80 degrees centigrade.

5. The method of claim 4, wherein the operation temperature of dispersing the color lake powder in water and adjusting the pH value of the reacting system to the range of 4 to 5.5 is 80 degrees centigrade.

6. The method of claim 1, wherein in step 3), washing the solid phase until an electric conductivity of a washing solution is less than 50 μS/cm.

7. The method of claim 1, wherein in step 2), a rotating speed of the blending is in a range of 300 r/min to 500 r/min, and a time of the blending is in a range of 100 min to 140 min.

8. The method of claim 1, wherein in step 3), a drying temperature is in a range of 80 degrees centigrade to 120 degrees centigrade.

* * * * *